(12) United States Patent
Muehlbauer et al.

(10) Patent No.: US 8,679,170 B2
(45) Date of Patent: Mar. 25, 2014

(54) METHODS AND APPARATUS FOR THERAPEUTIC APPLICATION OF THERMAL ENERGY

(75) Inventors: Thomas G. Muehlbauer, San Diego, CA (US); Nathan Newman, Beverley Hills, CA (US)

(73) Assignee: Avacen, Inc., San Diego, CA (US)

( * ) Notice: Subject to any disclaimer, the term of this patent is extended or adjusted under 35 U.S.C. 154(b) by 394 days.

(21) Appl. No.: 13/188,900

(22) Filed: Jul. 22, 2011

(65) Prior Publication Data
US 2012/0191022 A1 Jul. 26, 2012

Related U.S. Application Data

(60) Provisional application No. 61/367,315, filed on Jul. 23, 2010.

(51) Int. Cl.
*A61F 7/00* (2006.01)
*A61H 1/00* (2006.01)

(52) U.S. Cl.
USPC ................ 607/108; 607/111; 601/11; 601/15

(58) Field of Classification Search
USPC ............ 601/6, 11, 15–16, 148–152; 607/108, 607/111; 2/159, 161.6, 161.7, 161.8, 169
See application file for complete search history.

(56) References Cited

U.S. PATENT DOCUMENTS

| | | | |
|---|---|---|---|
| 1,399,095 A * | 12/1921 | Webb, Sr. ........................... 24/1 |
| 1,740,624 A | 12/1929 | Peel | |
| 4,329,997 A * | 5/1982 | de Yampert et al. .......... 607/114 |
| 4,735,195 A * | 4/1988 | Blum et al. ...................... 601/33 |
| 5,369,807 A * | 12/1994 | Cho et al. ........................... 2/159 |
| 5,683,438 A | 11/1997 | Grahn | |
| 5,688,208 A * | 11/1997 | Plemmons ...................... 482/44 |
| 5,693,004 A * | 12/1997 | Carlson et al. .................. 601/23 |
| 5,733,318 A | 3/1998 | Augustine | |
| 6,149,674 A | 11/2000 | Borders | |
| 6,315,696 B1 * | 11/2001 | Garrioch .......................... 482/49 |
| 6,434,423 B1 * | 8/2002 | Ross ................................. 607/2 |
| 6,602,277 B2 | 8/2003 | Grahn et al. | |

(Continued)

FOREIGN PATENT DOCUMENTS

| WO | WO-98/40039 | 9/1998 |
| WO | WO 03/007804 A2 | 1/2003 |
| WO | WO 2005/030101 A1 | 4/2005 |

OTHER PUBLICATIONS

Response to Written Opinion for PCT/US2011/044949, 4 pages, mailed May 3, 2012.

(Continued)

*Primary Examiner* — Justine Yu
*Assistant Examiner* — Christopher Miller
(74) *Attorney, Agent, or Firm* — Foley & Lardner LLP; Nicola A. Pisano; Christopher C. Bolten

(57) ABSTRACT

Apparatus and methods are provided for treating a human condition by providing an appendage chamber having a thermal exchange member. A vacuum may be applied to the appendage chamber to maintain vasodilation of an appendage when placed within the appendage chamber. The appendage may be heated or cooled at the thermal exchange member for therapeutic application of thermal energy to treat a number of circulatory, neurological, lymphatic, or endocrinal maladies.

23 Claims, 10 Drawing Sheets

(56) References Cited

U.S. PATENT DOCUMENTS

| | | | |
|---|---|---|---|
| 6,656,208 B2 | 12/2003 | Grahn et al. | |
| 6,673,099 B2 | 1/2004 | Grahn et al. | |
| 6,752,794 B2* | 6/2004 | Lockwood et al. | 604/313 |
| 6,846,322 B2* | 1/2005 | Kane et al. | 607/111 |
| 6,966,922 B2 | 11/2005 | Grahn et al. | |
| 6,974,442 B2 | 12/2005 | Grahn et al. | |
| 7,122,047 B2 | 10/2006 | Grahn et al. | |
| 7,160,316 B2 | 1/2007 | Hamilton et al. | |
| 7,169,119 B2* | 1/2007 | Chan et al. | 601/15 |
| 7,182,776 B2 | 2/2007 | Grahn et al. | |
| 7,862,600 B2 | 1/2011 | Grahn et al. | |
| 7,972,287 B2 | 7/2011 | Stewart et al. | |
| 8,460,355 B2 | 6/2013 | Cazzini et al. | |
| 2001/0049546 A1* | 12/2001 | Dvoretzky et al. | 607/108 |
| 2003/0040783 A1* | 2/2003 | Salmon | 607/111 |
| 2006/0111766 A1 | 5/2006 | Grahn et al. | |
| 2007/0060987 A1 | 3/2007 | Grahn et al. | |
| 2007/0093730 A1* | 4/2007 | Chan et al. | 601/15 |
| 2007/0112400 A1* | 5/2007 | Hamilton et al. | 607/104 |
| 2007/0123962 A1* | 5/2007 | Grahn et al. | 607/108 |
| 2007/0240247 A1* | 10/2007 | Beck | 2/16 |
| 2008/0021531 A1* | 1/2008 | Kane et al. | 607/111 |
| 2008/0034466 A1* | 2/2008 | Zicarelli | 2/158 |
| 2008/0077201 A1 | 3/2008 | Levinson et al. | |
| 2008/0077205 A1* | 3/2008 | Cazzini | 607/104 |
| 2008/0132816 A1 | 6/2008 | Kane et al. | |
| 2008/0132976 A1* | 6/2008 | Kane et al. | 607/104 |
| 2008/0208088 A1 | 8/2008 | Cazzini et al. | |
| 2009/0048649 A1* | 2/2009 | Peret et al. | 607/100 |
| 2009/0112298 A1 | 4/2009 | Jusiak et al. | |
| 2009/0177184 A1 | 7/2009 | Christensen et al. | |
| 2009/0240191 A1 | 9/2009 | Loori et al. | |
| 2010/0106230 A1 | 4/2010 | Buchanan et al. | |
| 2010/0152633 A1* | 6/2010 | Rein et al. | 601/152 |
| 2010/0262048 A1* | 10/2010 | Shinomiya et al. | 601/35 |
| 2011/0172749 A1 | 7/2011 | Christensen et al. | |

OTHER PUBLICATIONS

International Preliminary Report on Patentability for PCT/US2011/044949, 8 pages, mailed Jul. 2, 2012.

Grahn et al., "Recovery from mild hypothermia can be accelerated by mechanically distending blood vessels in the hand," J. Appl Physiol. vol. 85 No. 5, pp. 1643-1648 (1998).

Written Opinion for PCT/US2011/044949, 7 pages, mailed Oct. 14, 2011.

International Search Report for PCT/US2011/044949, 5 pages, mailed Oct. 14, 2011.

* cited by examiner

METHODS AND APPARATUS FOR THERAPEUTIC APPLICATION OF THERMAL ENERGY

I. CROSS-REFERENCE TO RELATED APPLICATIONS

This application claims the benefit of priority of U.S. provisional application Ser. No. 61/367,315, filed Jul. 23, 2010, the entire contents of which are incorporated herein by reference.

II. FIELD OF THE INVENTION

This application generally relates to therapeutic manipulation of mammalian thermoregulation.

III. BACKGROUND OF THE INVENTION

The body temperature of mammals is normally tightly controlled by an autonomic regulatory system referred to herein as the thermoregulatory system. A primary effector of this regulatory system is blood flow to specialized skin areas where heat from the body core may be dissipated to the environment. Normally, when body and/or environmental temperatures are high, the dilation of certain blood vessels favors high blood flow to these surfaces, and as environmental and/or body temperatures fall, vasoconstriction reduces blood flow to these surfaces and minimizes heat loss to the environment.

Strategic inducement of vasodilation in targeted portions of the body, such as the extremities, may exert positive therapeutic benefits in remote regions of the body. For example, manipulating heat transfer across the skin may change the core temperature of the mammalian body in response. Unfortunately, it may be difficult to induce such changes to an extent sufficient for therapy, given the human body's refined ability to thermoregulate to maintain temperature homeostasis or normothermia.

Applying heat and subatmospheric (negative) pressure to a hypothermic individual's skin, increases in body core temperature may be achieved (see, e.g., Grahn et al., "Recovery from mild hypothermia can be accelerated by mechanically distending blood vessels in the hand," J. Appl Physiol. (1998) 85(5):1643-8). Other therapeutic applications for cooling the skin have also been described; e.g., in treating cancer as described in U.S. Pat. No. 7,182,776 to Grahn. However, therapeutic applications for continuously applying heat to the skin after the core body temperature reaches, or is at, normothermia to increase microvascular circulation to treat conditions whose symptoms may include pain and inflammation have not been demonstrated.

U.S. Pat. No. 7,160,316 to Hamilton describes apparatus and methods for regulating body core temperature using an appendage chamber having a heat exchange element and configured to maintain vacuum conditions. The appendage chamber includes a strap to secure a person's hand on the heat exchange element. In practice, such a strap does not accommodate hands of different sizes: the strap may be too loose on small hands and may cause vasoconstriction of the arteriovenous anastomosis vascular area in the palm of large hands because the palm is pressed too hard against the heat exchange element. Additionally, the appendage chamber includes a hand seal configured to seal an appendage within the appendage chamber. Such a hand seal may cause leakage and does not provide the proper characteristics for maintaining a vacuum in the appendage chamber.

U.S. Pat. No. 6,846,322 to Kane describes apparatus and methods for manipulating body core temperature using an appendage chamber configured to maintain vacuum conditions. The appendage chamber includes a first flexible member and a first energy element disposed in an upper portion of the appendage chamber and a second flexible member and a second energy element disposed in a lower portion of the appendage chamber. The first flexible member is configured to enhance the surface contact between the first energy element and an upper portion of an appendage placed within the appendage chamber while the second flexible member is configured to enhance the surface contact between the second energy element and a lower portion of the appendage. The system described in Kane suffers from a number of drawbacks, including the use of multiple elements for delivering thermal energy to the appendage, thereby increasing manufacturing cost and complexity, and providing multiple failure modes.

In view of the foregoing drawbacks of previously known systems, it would be desirable to provide a robust and economical system for effecting whole body heating to increase whole body circulation.

IV. SUMMARY OF THE INVENTION

The present invention overcomes the drawbacks of previously-known apparatus by providing apparatus including an appendage chamber, a thermal exchange member, a pressure platform, a tubular sleeve, a vacuum source, a heating or cooling source, and a programmable controller. The appendage chamber may be configured to accept a human hand and has upper and lower portions and an appendage opening having a rim. The thermal exchange member may be disposed within the lower portion and may be configured to contact a palm of the hand. The pressure platform may be disposed under the thermal exchange member and may be configured to measure a pressure of the hand against the thermal exchange member. The tubular sleeve may have first and second open ends and be configured to accept a human arm. One of the first and second ends may be disposed over the rim. The vacuum source may be coupled to the appendage chamber to maintain vasodilation of the hand when placed within the appendage chamber and the heating or cooling source may be coupled to the thermal exchange member. The programmable controller may be configured to monitor the pressure measured using the pressure platform, to control the application of vacuum to the appendage chamber, and to control heating or cooling of the thermal exchange member to effect heating or cooling responsive to a preselected therapy regime.

The apparatus may further include an inflatable bladder disposed within the upper portion and configured to selectively urge the hand against the thermal exchange member with a force sufficient to provide satisfactory heat transfer, but without causing vasoconstriction. The programmable controller may be further configured to inflate the inflatable bladder to a preselected pressure.

The apparatus may be configured to heat or cool a normothermic person, e.g., a person having a normal body temperature, or a sub-normothermic or a hyper-normothermic person. The apparatus may heat or cool the appendage at a temperature and for a duration sufficient to increase whole body circulation, e.g., microvascular circulation. In accordance with one aspect of the present invention, such increased systemic flow may induce redistribution of blood flow in other body regions. For example, increased systemic flow may cause a redistribution of intracranial flow that alleviates symptoms associated with neurological maladies, such as migraine headaches.

The apparatus also may heat or cool the appendage at a temperature and for a duration sufficient to increase whole body circulation, e.g., microvascular circulation, to stimulate other body defensive or healing mechanisms, such as by stimulating activity within the lymphatic system. In accordance with one aspect of the present invention, such increased circulation may promote exudate generation at a remote site of a chronic wound to promote wound healing.

The apparatus additionally may heat or cool the thermal exchange member to deliver normothermic heating or cooling to the appendage at a temperature and for a duration sufficient to alleviate symptoms associated with a deficiency in the endocrine system. In accordance with one aspect of the present invention, increased circulation resulting from normothermic increases in body core temperature may enhance endocrine response, such as stimulating or suppressing hormone generation and release associated with thyroid deficiencies, or ovulation or menstrual cycles.

Methods of using the apparatus of the present invention to treat a variety of medical conditions also are provided.

V. BRIEF DESCRIPTION OF THE DRAWINGS

FIGS. 1A and 1B, respectively, are perspective views of an exemplarily apparatus for treating a condition in a closed position (FIG. 1A) and open position (FIG. 1B).

VI. DETAILED DESCRIPTION OF THE INVENTION

The present invention provides methods and apparatus for applying thermal energy to a human to increase or rebalance blood circulation, and/or stimulate the lymphatic or endocrine systems to address a variety conditions. The methods and apparatus of the present invention are expected to provide beneficial results in treating a number of common ailments, including improved healing of chronic wounds, and relief from neurological and hormone-relating ailments.

In accordance with one aspect of the present invention, an apparatus is provided that includes an appendage chamber, a vacuum source, and a thermal exchange member. In one embodiment, the apparatus provides a negative pressure environment that maintains vasodilation of an arteriovenous anastomosis vascular area of the palm of a human hand. The arteriovenous anastomosis vascular area may experience vasodilation from pre-treatment hyper-normothermia and/or heat delivered to the area from the thermal exchange member during treatment. This vasodilation increases the heat exchange between the thermal exchange member and the body core by increasing blood flow between the palm and the body core. An appendage chamber, e.g., clam shell, glove-like, boot-like, or sleeve-like chamber, may be used to provide a negative pressure environment while providing heat to an appendage using a thermal exchange system for a preselected time, e.g., between approximately 5 and 20 minutes. While embodiments of the invention will be described further below with respect to a chamber configured to receive a hand, it is recognized that the appendage chamber may be adapted for use with other vasculatures suitable for the vasodilation methods described herein, such as vasculatures in the head, arm, foot, and/or leg.

Apparatus Overview

Figure 1A:
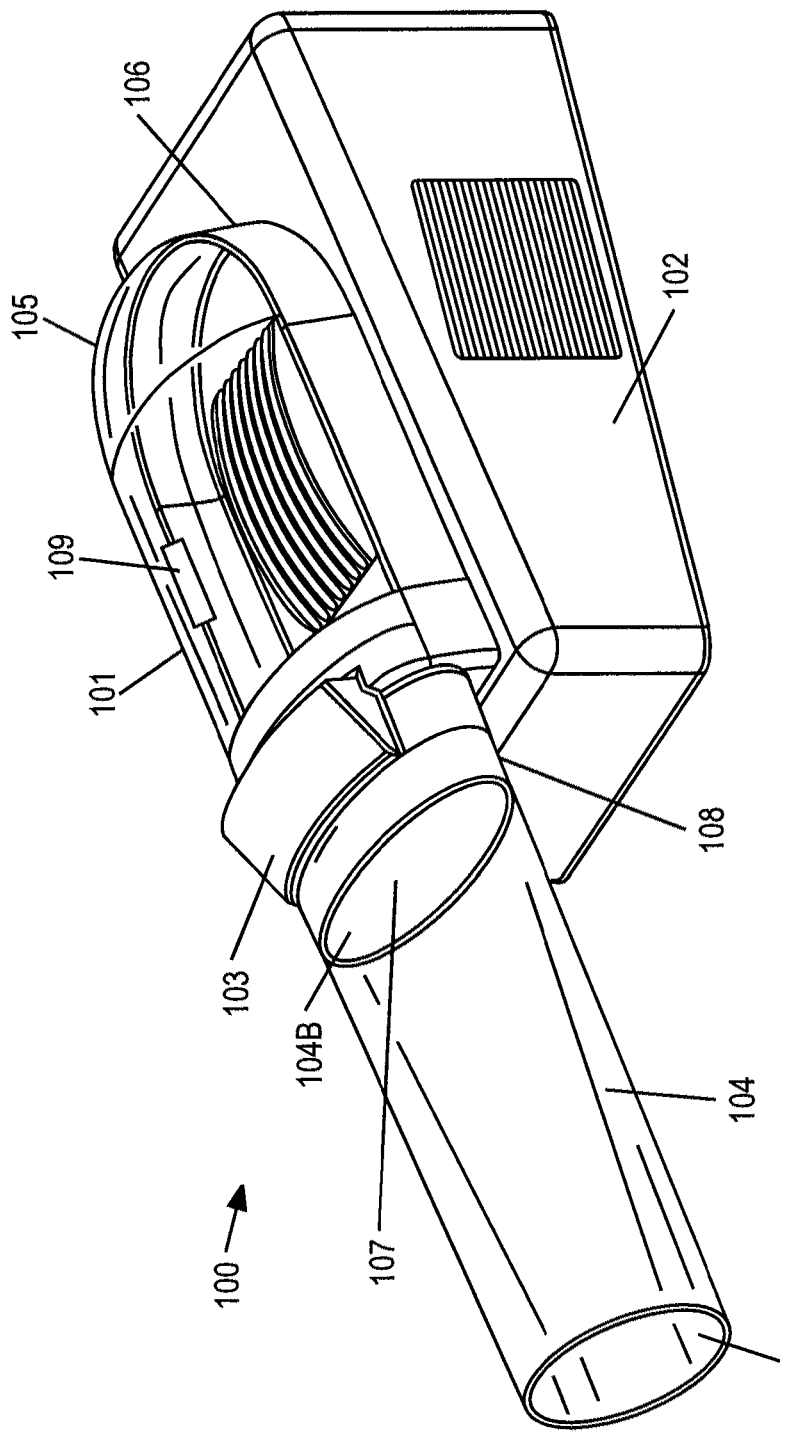
Figure 1B:
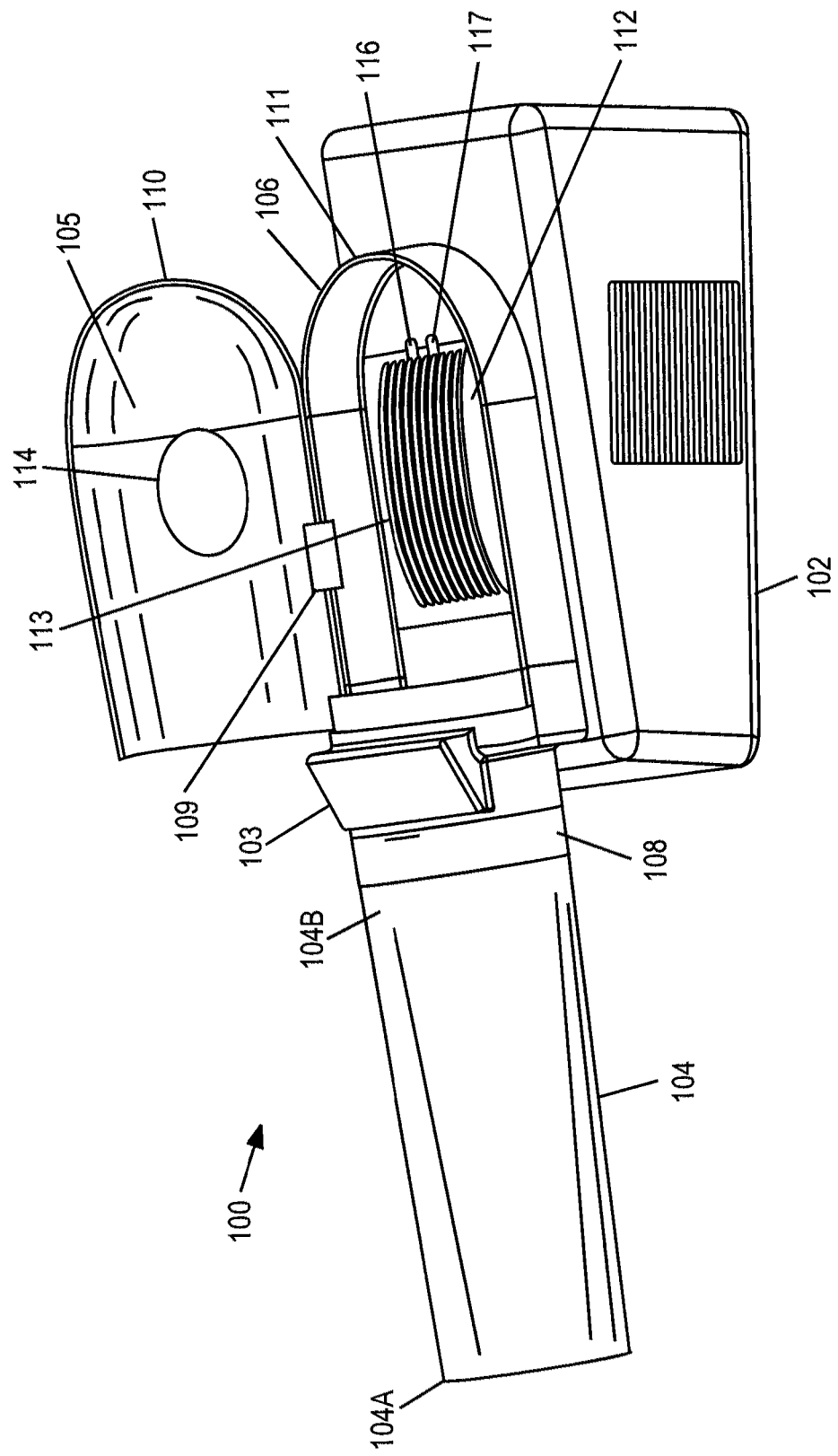

Referring to FIGS. 1A and 1B, apparatus 100 for treating a condition is provided, including appendage chamber 101, housing 102, control panel 103, and optional tubular sleeve 104. Appendage chamber 101 may be configured to accept a human hand and includes upper portion 105 and lower portion 106. Upper portion 105 may be partially or fully transparent such that a user and/or physician may monitor the hand during treatment. In one embodiment, upper and lower portions 105 and 106 may be pivoted open and closed using hinge 109. In this embodiment, upper and/or lower portions 105 and 106 may further include fasteners, e.g., quick-release buckles or VELCRO® straps, that fasten the portions together when appendage chamber 101 is closed. In an alternative embodiment, upper and lower portions 105 and 106 may be integrated. Appendage chamber 101 further includes appendage opening 107 having rim 108 and configured to accept the human hand.

Appendage chamber 101 may be coupled to housing 102 having a programmable controller, a heating or cooling source, and a vacuum source provided therein, which are activated responsive to commands input via control panel 103. The vacuum source is configured to create a vacuum in appendage chamber 101 when an appendage is placed therein to maintain vasodilation of an arteriovenous anastomosis vascular area of the appendage, e.g., located in the palm of a hand. The arteriovenous anastomosis vascular area may experience vasodilation from pre-treatment hyper-normothermia and/or heat delivered to the area from thermal exchange member 113, shown in FIG. 1B, during treatment. The heating or cooling source is configured to circulate a heating or cooling medium to appendage chamber 101 to heat or cool the appendage under vacuum conditions, thereby increasing heat exchange between apparatus 100 and a human's body core.

As depicted in FIG. 1B, apparatus 100 may be moved to an open position by pivoting upper portion 105 on hinge 109. Upper portion 105 may have upper rim 110 suitably sized such that upper rim 110 fits within lower rim 111 of lower portion 106 when appendage chamber 101 is closed. Lower portion 106 of appendage chamber 101 preferably includes pressure platform 112 and thermal exchange member 113 configured to contact a palm of the hand. Pressure platform 112 is configured to measure a pressure of the hand against thermal exchange member 113 and may include a pressure sensor, e.g., pressure transducer or load cell, to measure the pressure. Pressure platform 112 may further include a built-in elastic band or an attached VELCRO® strap configured to secure a hand to thermal exchange member 113 on pressure platform 112. Thermal exchange member 113 may be disposed on pressure platform 112 and is operatively coupled to the cooling or heating source such that the cooling or heating medium may be circulated to cool or heat thermal exchange member 113. Advantageously, pressure platform 112 and thermal exchange member 113 are configured to accommodate many different sizes of hands, including those of unconscious patients, while minimizing the risks of discomfort or vasoconstriction. Additionally, the pressure measured at pressure platform 112 may be used to determine if a hand is placed too lightly on thermal exchange member 113, thereby reducing heat transfer, or placed too heavily, thereby inducing vasoconstriction of the vasculature of the palm. As explained below, an alert at control panel 103 may be audibly or visibly displayed if the measured pressure is not within a predetermined range, e.g., too high or too low.

In accordance with one aspect of the present invention, upper portion 105 of appendage chamber 101 includes optional inflatable bladder 114, which is configured to selectively urge a hand against thermal exchange member 113. Inflatable bladder 114 may be inflated to a preselected pressure, e.g., 3 lbs. per square inch, to assure that the palm is comfortably pressed against the thermal exchange member 113 without causing vasoconstriction of the vasculature in the palm. Advantageously, inflatable bladder 114 is configured to accommodate many different sizes of hands, including those of unconscious patients, without causing discomfort or vasoconstriction. As described in greater detail below, the single bladder construction of the system depicted in FIG. 1B enables both large and small hands to be disposed within chamber 101, such that small hands are urged with sufficient pressure against thermal exchange member 113 to effect satisfactory heat transfer, while larger hands are not pinned so tightly as to induce vasoconstriction of the vasculature of the palm.

In preferred embodiments, appendage chamber 101 comprises a durable and relatively rigid plastic or metal alloy, or combination thereof, of which individual components may be formed using conventional injection-molding or stamping processes. Preferably, upper portion 105 of chamber 101 comprises a rigid, substantially transparent plastic or polymer, such as polycarbonate, which allows the user or caregiver to visualize placement of the hand within the chamber.

Figure 2A:
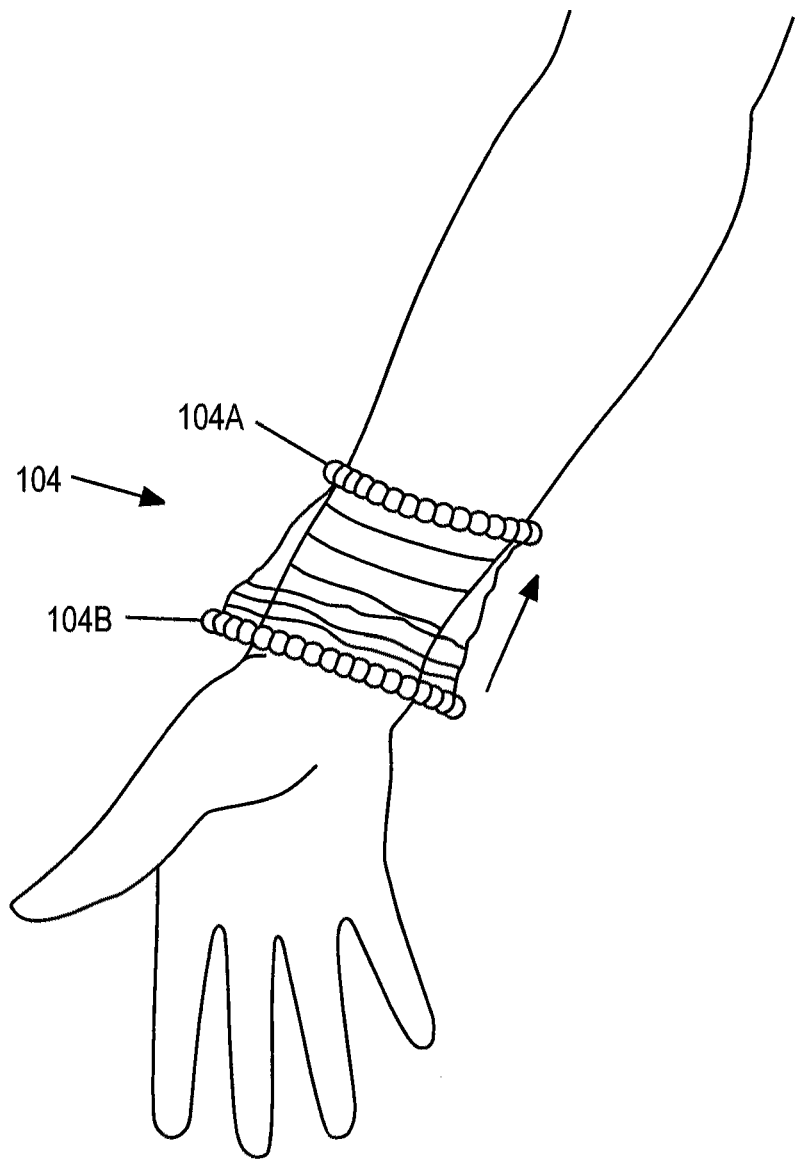
FIGS. 2A and 2B depict alternative embodiments of a tubular sleeve worn on a human arm for use with the apparatus of FIGS. 1A and 1B.

Referring now to FIG. 2A, a first embodiment of tubular sleeve 104 suitable for use with apparatus 100 is described. Tubular sleeve 104 may be detachably coupled to appendage chamber 101 and have first end 104A and second end 104B, each suitable sized to receive an appendage, illustratively an arm. First and/or second ends 104A and 104B may include a built-in elastic band or an attached VELCRO® strap. Second end 104B preferably is sized to be disposed over rim 108 when a hand is placed within appendage chamber 101. Then, when the vacuum source coupled to the interior of chamber 101 applies a vacuum, a portion of tubular sleeve 104 is drawn tightly around the arm and into appendage opening 107 to create a substantially airtight seal within appendage chamber 101 sufficient to maintain vasodilation of the enclosed appendage. Sleeve 104 may comprise a flexible and durable material, such as neoprene, that may be used with different patients. Alternatively, sleeve 104 may be disposable and designed for one-time use. In this case, sleeves 104 of having different sizes may be supplied with apparatus 101 to reduce cross-contamination if the device is used by multiple patients.

Figure 2B:
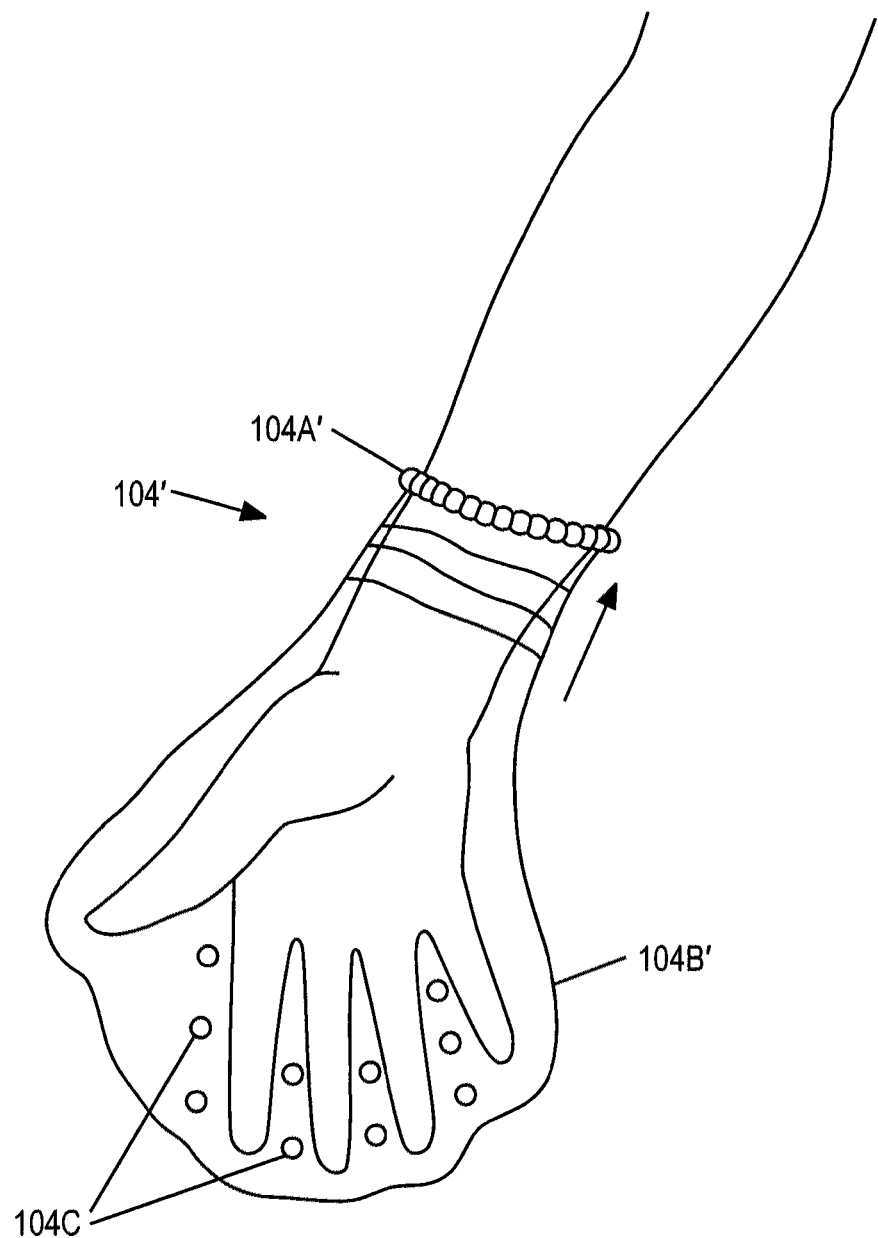

FIG. 2B depicts an alternative embodiment of a tubular sleeve designed to further reduce cross-contamination by entirely covering the appendage placed in chamber 101. Tubular sleeve 104' preferably comprises a light weight plastic, such as polyethylene, and is disposable after a single use. For this embodiment, tubular sleeve includes first end 104A' that is designed to slip over an appendage, such as an arm, while second end forms a pouch or mitt 104B'. A plurality of holes 104C are disposed in the portion of mitt 104B' that contacts the back of the fingers. When the appendage is placed within chamber 101, and the vacuum source is activated, first end 104A' of the tubular sleeve 104' will be drawn down on the arm to occlude opening 107, thereby providing a substantially airtight seal for chamber 101. Any air trapped within mitt 104B' will be drawn out from within tubular sleeve 104' through holes 104C, thereby causing mitt 104B' also to be drawn tightly around the hand. Provided that the material comprising sleeve 104' is sufficiently thin, tubular sleeve 104' is expected to provide adequate heat transfer between the palm of the hand and thermal exchange member 113, while reducing the potential for spread of bacteria or viruses in cases where multiple users use apparatus 100, such as hospital or nursing home settings.

Figure 3A:
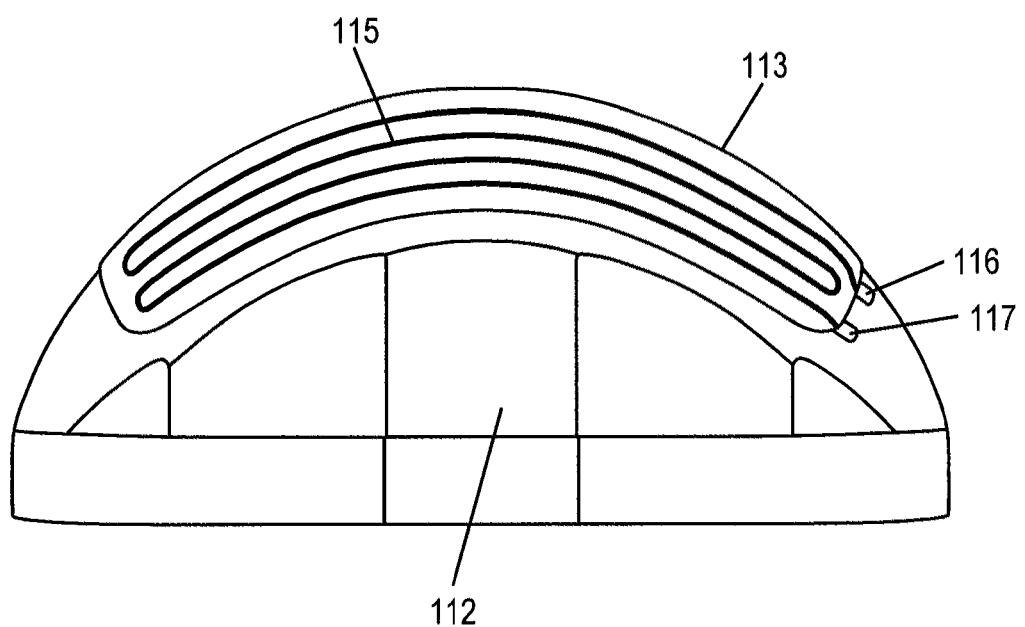
FIGS. 3A and 3B are side and exploded views, respectively, of an exemplary thermal exchange member and pressure platform for use in an apparatus of the present invention.
Figure 3B:
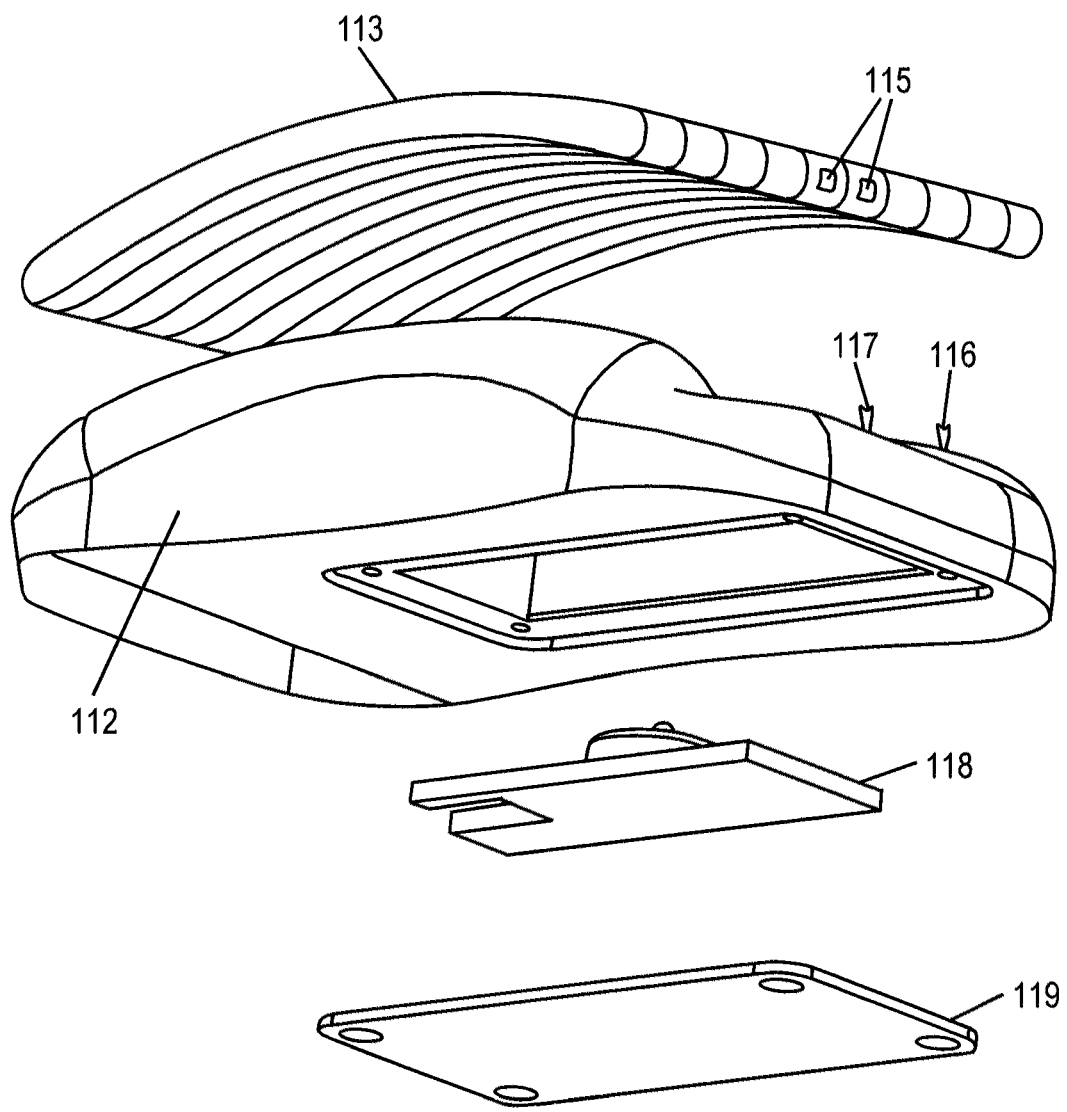

Referring now to FIGS. 3A and 3B, thermal exchange member 113 is described, including at least one channel 115, medium inlet 116, and medium outlet 117. In one embodiment, thermal exchange member 113 comprises a flexible, e.g., plastic, bag having a plurality of channels. Thermal exchange member 113 preferably is made from a material capable of transferring heat to or from the palm of a human hand, and may comprise a flexible and durable material, such as neoprene and may be disposable after a single use or a biocompatible metal, such as aluminum, or metal alloy. A pump disposed in housing 102 may be used to pump a heating or cooling medium, e.g., water, from a heating or cooling source into medium inlet 116. The medium circulates through channel 115 and exits via medium outlet 117. Inlet 116 and outlet 117 may be in the form of a quick puncture attachment that opens access to prefilled and sealed channel 115.

Thermal exchange member 113 may be supported on pressure platform 112, which may comprise a light weight thermally insulating member to reduce thermal inertia and overall weight of the device. Pressure platform 112 may include pressure sensor 118 and cover 119 as shown in FIG. 3B. Pressure sensor 118 is a suitable pressure sensor, e.g., pressure transducer or load cell, and is configured to measure a pressure and/or force that an appendage applies to pressure platform 112. Cover 119 may be configured to hold pressure sensor 118 within pressure platform 112.

Figure 4A:
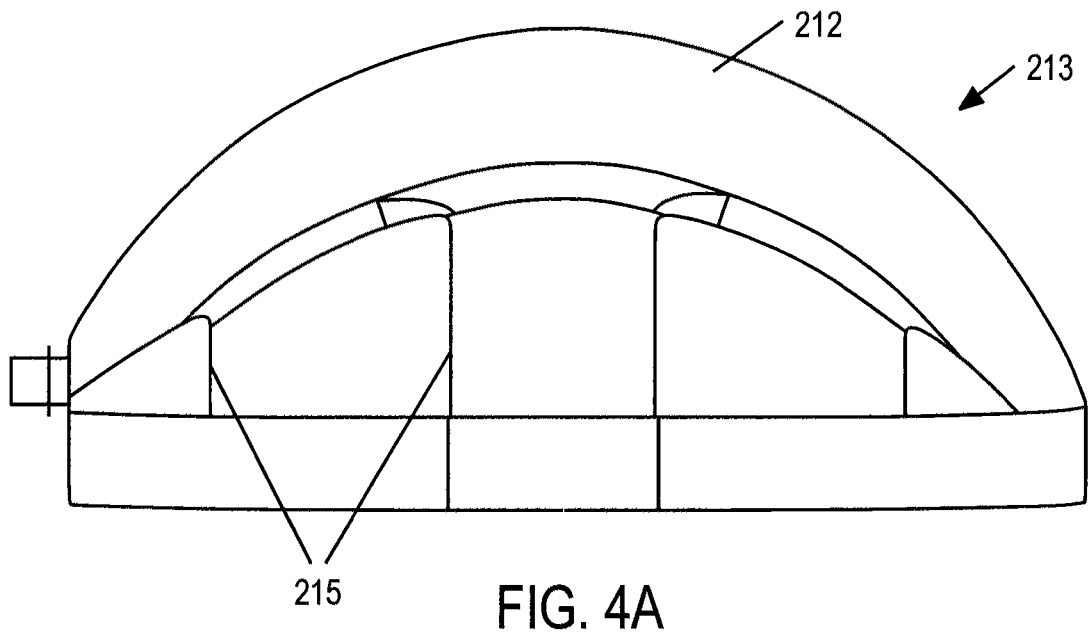
FIGS. 4A and 4B are side and perspective views, respectively, of an alternative thermal exchange member with optional pressure platform for use in an apparatus of the present invention.
Figure 4B:
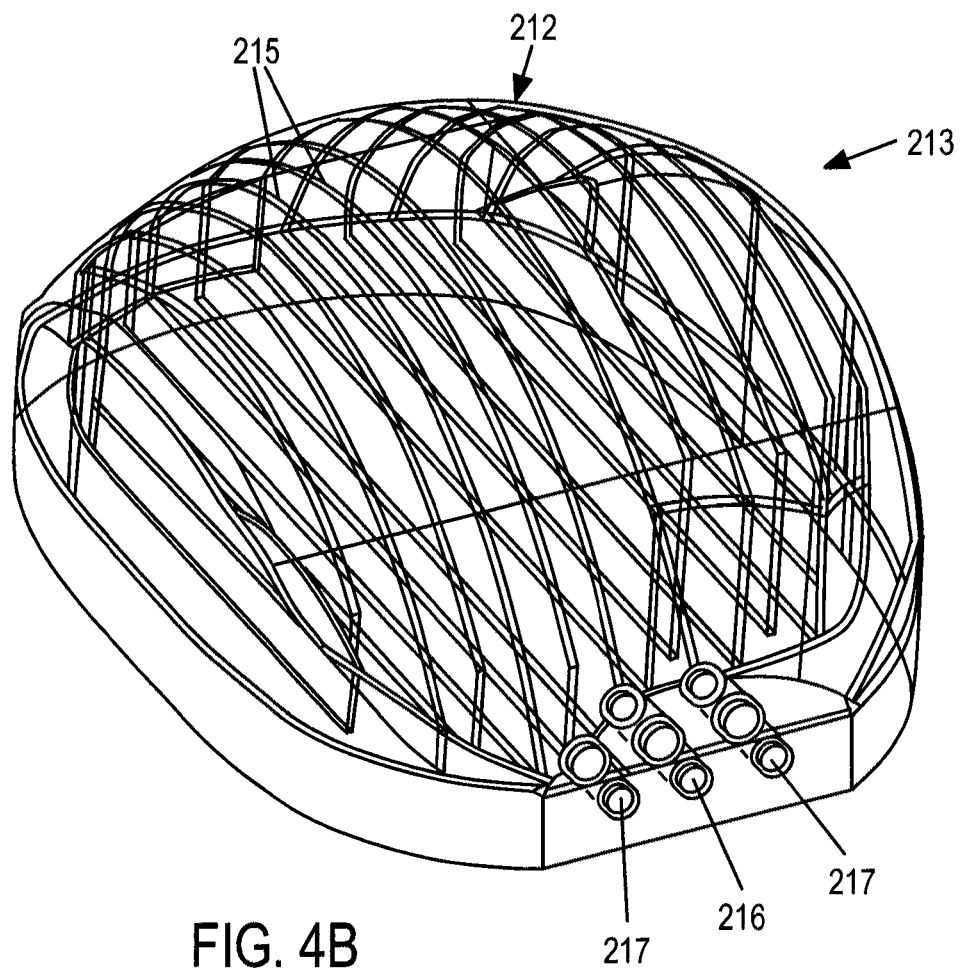

FIGS. 4A and 4B depict an alternative embodiment of thermal exchange member 213, plurality of channels 215, medium inlet 216, and medium outlets 217, and disposed on or integral with pressure platform 212. A pump disposed in housing 102 may be used to pump a heating or cooling medium, e.g., water, from a heating or cooling source into medium inlet 216. The medium then circulates through plurality of channels 215 to heat or cool thermal exchange member 213 and drains to an exhaust manifold connected to medium outlets 217. Thermal exchange member 213 preferably is made from a material capable of transferring heat to or from the palm of a human hand, and may comprise a biocompatible metal, such as aluminum, or metal alloy. So as to reduce the thermal inertia of thermal exchange member 213, member 213 may comprise mating cast or stamped concave surfaces, and be supported on an insulating support structure. In this manner, thermal exchange member 213 preferably can reach its operating temperature rapidly once the heating or cooling medium is introduced, while the use of a light weight insulating support reduces the overall weight of chamber 101. Pressure platform 212 may further include a pressure sensor similar to pressure sensor 118, described above.

Figure 5:
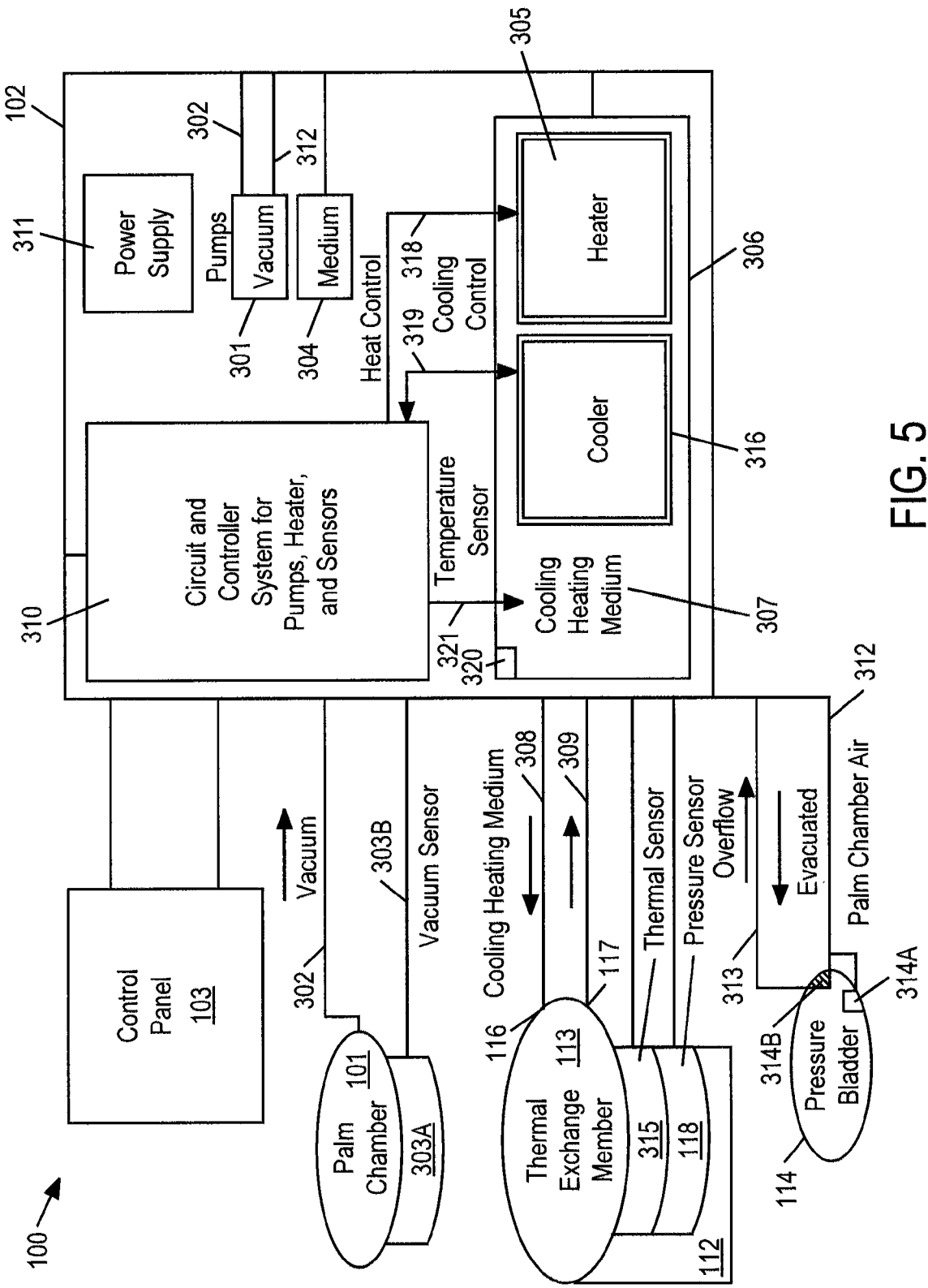
FIG. 5 is a schematic view of an apparatus for treating a condition using thermal energy constructed in accordance with one aspect of the present invention.

Referring now to FIG. 5, a schematic illustrating the internal components of the embodiment of apparatus 100 is described. In this embodiment, housing 102 contains the electronics and mechanical systems, e.g., heating or cooling system and vacuum system, required to regulate temperature and pressure within chamber 101. Housing 102 preferably includes vacuum pump 301, medium pump 304, heater 305, heating or cooling source 306, including heating or cooling medium 307, programmable controller 310, power supply 311, and cooler 316. The electronics disposed in housing 102 are coupled to control panel 103, so that programmable controller 310 actuates apparatus 100 in accordance with input commands or selection of pre-programmed therapy regimes input via control panel 103.

Vacuum source 301 is configured to create a vacuum in appendage chamber 101 at a suitable pumping rate, e.g., greater than about 4 liters per minute, to maintain vasodilation of a human palm disposed within chamber 101. In one embodiment, vacuum source 301 may be a diaphragm pump coupled to appendage chamber 101 via vacuum line 302. Vacuum sensor 303A may be coupled to appendage chamber 101. Vacuum sensor 303A is configured to sense the pressure within appendage chamber 101 and to output a signal to programmable controller 310, via line 303B or wirelessly, that is used to achieve a preselected vacuum, e.g., between 25 mm Hg to 35 mm Hg, within chamber 101. Outlet 312 of vacuum source 301 may dispose of air that has been exhausted by vacuum source 301. In an embodiment where apparatus 100 includes inflatable bladder 114, outlet 312 of vacuum source 301 may be coupled to inflatable bladder 114 such that inflatable bladder 114 may be inflated using gas, e.g., air, that has been exhausted by vacuum source 301. Air pressure within bladder 114 may be monitored by pressure sensor 314A, which has an output coupled to programmable controller 310. In this manner, outlet 312 of vacuum source 301 may be selectively connected, responsive to programmable controller 310, to bladder 114 to maintain a preselected pressure in inflatable bladder 114, e.g., 3 psi. Programmable controller 310 also may be coupled to bladder pressure valve 314B, such that controller 310 operates valve 314B to open to redirect gas pumped from outlet 312 to bladder overflow outlet 313 once bladder 114 has attained a predetermined target pressure, as monitored by pressure sensor 314A.

Medium pump 304 is configured to pump heating or cooling medium 307 from heating or cooling source 306 to thermal exchange member 113 through medium inlet 308 and out through medium outlet 309. Heating or cooling source 306 may include heater 305 that is configured to heat medium 307. Heater 305 may be a suitable electric heater, e.g., a resistor heater, and may be submerged in cooling or heating source 306. In one embodiment, thermal exchange member 113 includes temperature sensor 315, e.g., a thermocouple, disposed adjacent to or within thermal exchange member 113 or pressure platform 112. Temperature sensor 315 is configured to sense a temperature at thermal exchange member 113. Sensor 315 may be operatively coupled to programmable controller 310 to regulate operation of medium source 304 to maintain thermal exchange member 113 at substantially a target temperature that may be preprogrammed or input via control panel 103.

In one embodiment, where medium 307 is to be heated, heater 305 is configured to heat medium 307 to a temperature such that thermal exchange member 113 is heated to approximately 43° C. as measured by medium temperature sensor 320. Medium temperature sensor 320 is a suitable temperature sensor, e.g., a thermocouple, configured to sense a temperature of medium 307 and may be disposed adjacent to or within heating or cooling source 306. Programmable controller 310 may control heater 305 via heat control line 318 or wirelessly based on measurements from sensor 320 communicated via temperature sensor line 321 or wirelessly. In an embodiment where medium 307 is to be cooled, cooler 316 may be used to cool medium 307 to a suitable temperature. Cooler 316 may be submerged within heating or cooling source 306 and programmable controller 310 may control cooler 316 via cooling control line 319 or wirelessly based on measurements from sensor 320 communicated via temperature sensor line 321 or wirelessly. Cooler 316 may include a Peltier device, a desiccant cooling device, or may be configured to generate an endothermic or exothermic chemical reaction to provide a temperature variance. In a preferred embodiment, heating or cooling medium 307 travels through apparatus 100 in a closed loop configuration. A closed loop configuration may reduce the maintenance requirements for a user because a closed loop minimizes the loss of heating or cooling medium 307 that generally occurs if heating or cooling source 306 is detached from apparatus 100. A closed loop configuration may also minimize contamination of heating or cooling medium 307.

Programmable controller 310 may employ a commercially available microcontroller, and is programmed to control vacuum source 301, medium pump 304, pressure monitoring at pressure platform 112, regulation of the temperature of thermal exchange member 113, and inflation and deflation of bladder 114. Programmable controller 310 may be configured to monitor a pressure that an appendage applies to pressure platform 112 as measured, for example, by pressure sensor 118. Pressure sensor 118 is a suitable pressure sensor, e.g., pressure transducer or load cell, and is configured to measure a pressure and/or force that an appendage applies to pressure platform 112. Programmable controller 310 may determine if the measured pressure and/or force is within a predetermined range and may cause control panel 103 to alert a user/caregiver/physician if the measured pressure and/or force is not within the predetermined range. For example, control panel 103 may alert a user/caregiver/physician that the force applied to pressure platform is less than 2 lbs.

Programmable controller 310 also is configured to control application of vacuum to appendage chamber 101 by controlling the pumping rate of vacuum source 301 and monitoring the conditions, e.g., pressure, of the vacuum sensor 303A disposed in or on appendage chamber 101. Programmable controller 310 further is configured to control heating or cooling of thermal exchange member 113 to effect normothermic, approximately 36 to 38° C. (97 to 100° F.) body temperature, heating or cooling responsive to a preselected therapy regime. In one embodiment, programmable controller 310 is configured to control heating or cooling of thermal exchange member 113 to determine if thermal exchange member 113 exceeds a predetermined temperature, e.g., 43° C. Programmable controller 310 may control the pump rate of medium pump 304, the output of heater 305, and also may monitor pressure platform sensor 118, bladder pressure sensor 314A, temperature sensor 315, and medium temperature sensor 320.

Programmable controller 310 may be configured to inflate inflatable bladder 114 to a preselected pressure when activated by control panel 103, based on pressure signals obtained from sensor 314A. In addition, chamber 101 also may include a limit sensor associated with hinge 109 that signals programmable controller 310 to inflate bladder 114 when upper portion 105 engages lower portion 106.

As described in greater detail below, programmable controller 310 may include a non-volatile memory for storing therapy programs directed to treatment of specific maladies. For example, an embodiment of apparatus 100 intended for use in a nursing home setting may include programs for increasing whole body circulation to address neurological ailments, such as migraine headaches, or circulatory issues, such as chronic wounds or reduced peripheral blood flow resulting from diabetes or immobility. In this context, apparatus may be used by a number of nursing home residents to provide relief from such ailments, and include preprogrammed therapeutic regimes (e.g., appropriate temperature adjustments for preselected durations) suitable for treating such residents. Programmable controller 310 preferably also includes preprogrammed safety features, e.g., that shutdown the device if the apparatus sensors, such as the temperature and pressure sensors, fail or become disconnected. Programmable controller 310 also may include an error circuit that displays error codes on control panel 103.

Power supply 311 is configured to power apparatus 100. Power supply 311 may be a suitable AC, DC, or combination power source known in the art. In a preferred embodiment, power supply 311 includes rechargeable batteries.

In alternative embodiments, one or more of the components supplied within housing 102 may be omitted. For example, an embodiment of apparatus 100 suitable for use in a hospital, where suction lines are readily available in the patient rooms, may omit vacuum source 301 and instead use the "house" suction system, although the operation of bladder valve 314B and vacuum generated in chamber 101 still would be controlled by programmable controller 310.

Figure 6:
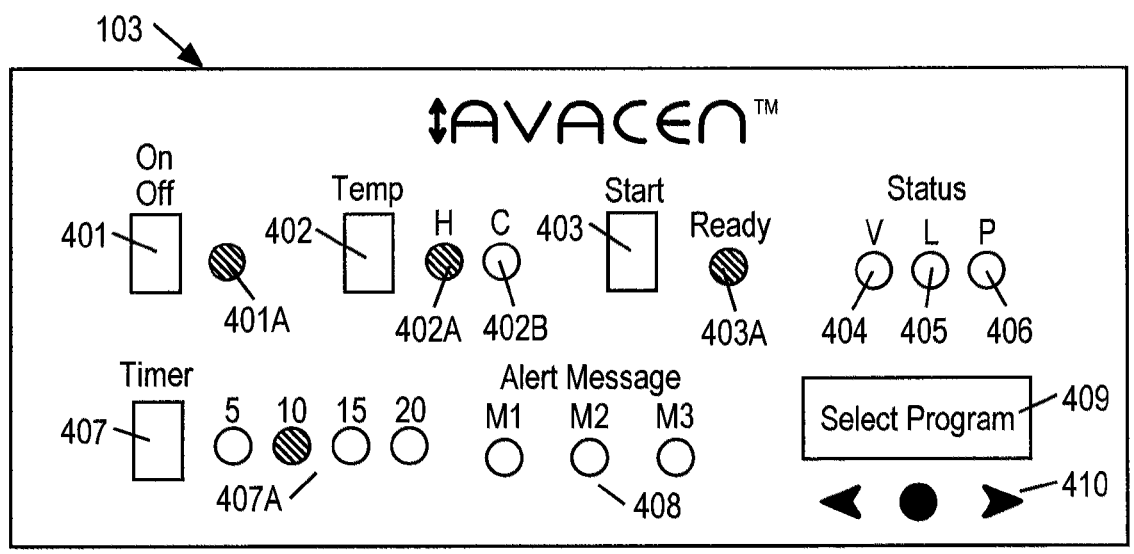
FIG. 6 depicts an exemplary control panel for use in an apparatus of the present invention.

Referring now to FIG. 6, an exemplary control panel 103 is described. Control panel 103 is configured to provide a user interface for a user and/or clinician or care-giver to control operations of apparatus 100. Control panel 103 may include On/Off button 401, Temp button 402, Start button 403, Timer button 407 and assorted lighting sources e.g., LEDs. Control panel 103 may be operatively coupled to programmable controller 310 of FIG. 5 such that programmable controller 310 controls the pumps, heater, cooler, and/or sensors of the apparatus based on user input received at control panel 103. Control panel 103 also may include optional display screen 409, e.g., an LCD or LED readout, that displays a preselected program selected using optional "Left" and "Right" buttons 410. Preselected programs stored in apparatus 100 may be loaded at the manufacturer, or generated using a suitable software program on a conventional personal computer and then uploaded to memory associated with programmable controller 310 via a data port, e.g., USB port, on housing 102.

Pushing On/Off button 401 activates power supply 311 and turns on LED 401A to indicate that the apparatus is powered on. After the controller power is activated, the system may default to heating mode indicated by heating H LED 402A. If Temp button 402 is pushed once within a predetermined time, e.g., 5 seconds, of receiving power, cooling C LED 402B will light and associated cooling functions will be activated. The apparatus may be switched between heating and cooling using Temp button 402. Leaving the unit in heating mode or cooling mode for a preselected time, e.g., more than 5 seconds, may activate the associated functions. Once heating or cooling mode is activated, the apparatus will heat or cool the heating or cooling medium. When the medium reaches a predetermined temperature, e.g., about 44° C. in heating mode, Ready LED 403A will light indicating that the apparatus is ready to start. The number of operating minutes then may be selected using Timer button 407. Illustratively, times of 5, 10, 15, or 20 minutes may be selected; however, the scope of the invention is not limited to these times. In one embodiment, if Timer button 407 is not pressed, a default of 10 minutes is used. Treatment then may be automatically started or may be started by pressing Start button 403.

During treatment, the apparatus may monitor characteristics such as vacuum pressure, inflatable bladder pressure (if present), pressure plate pressure, medium temperature, and thermal exchange member temperature. Status LEDs 404, 405, and 406 may be used to indicate a number of conditions of the apparatus. For example, "V" Status LED 405 may be lit if the vacuum within the appendage chamber drops below 25 mm Hg and the vacuum source may turn off after a predetermined time, e.g., 10 seconds, if the vacuum does not rise above 25 mm Hg. As another example, "L" Status LED 405 may be lit if the temperature sensor senses a temperature of 44° C. or higher at the thermal exchange member and the apparatus may automatically turn off the medium pump after a predetermined time, e.g., 20 seconds. As yet another example, "P" Status LED 406 may be lit if the pressure sensor in the pressure platform senses that a pressure applied thereto by an appendage is not within a predetermined range. The meanings of the different combinations of lit Alert Message LEDs 408 may be noted in the user manual.

If a feature is available to provide a pre-programmed therapy regime using optional buttons 410 and display 409, buttons 410 may be pushed to select a specific pre-determined program to control that activation of apparatus 100. In this case, selection of a pre-selected program using buttons 410 will select whether therapy is to be conducted with heating or cooling and the duration of the treatment, and thus may override operation of buttons 402 and 407 as described above.

Methods of Using the Apparatus

Methods of using apparatus for the therapeutic application of thermal energy will now be described with reference to FIGS. 1A through 6.

As the terms are used herein, "thermoregulatory system" refers to the autonomic regulatory system and components thereof that are responsible for temperature maintenance or control in a mammal, particularly maintenance and control of the core body temperature. As such, the thermoregulatory system that is involved in the subject methods is the one responsible for the control of the core body temperature of the mammal under various environmental conditions. Further, the term "manipulate" as applied to the thermoregulatory system of a mammal refers to a change or modulation in the system's response to environmental temperatures, where the nature of the change or modulation is generally to alter the thermoregulatory control and therefore state or status of the mammal in a manner that is not normal or observed in a control situation. In other words, manipulate is meant to cause the thermoregulatory state or status of the mammal to deviate from the level present at time of treatment according to the invention.

By "body core" is meant the internal body region or portion of the mammal, as opposed to the surface of the mammal, especially the internal core body region.

The thermoregulatory system is considered to be lowered from normal temperatures (or a at a sub-normothermic state) if temperatures of particular sites in the body core fall below normal ranges and/or temperature gradients between different sites of the body core exceed normal ranges. Normal temperature ranges for deep core body temperatures are generally from about 35 to 39 and usually 36 to 38° C., where the temperature of the core body is often 37° C. A normal gradient between any two sites in the body core, e.g., between the brain and the heart, brain and abdomen, etc., is generally not greater than about 2° C. in magnitude, usually not greater than about 1° C. in magnitude and often not greater than 0° C. in magnitude.

Despite the breadth of the "normal" range of temperatures in humans spanning as much as 35 to 39° C., for a given set of conditions, core temperatures lower than about 0.5 to 1.0 degree or more of 37° C. may be regarded as sub-normothermic or tending toward subnormothermia. Thus, for humans, "low" core body temperatures mean those less than about 36° C., more preferably less than about 35.5° C. or most preferably less than about 35° C. While practice of the invention is illustrated by application to humans, it is not so limited. Those of skill in the animal health field will be familiar with normal ranges of temperatures, and temperatures considered to be sub-normothermic, for other species of mammals, and should be able to practice the invention on such species accordingly.

By such application, the core body temperature of the mammal, if substantially normothermic at time of treatment, is maintained or, if substantially sub-normothermic at time of treatment, is substantially raised to normal levels. Thus, the amount of increase of core body temperature achieved in the subject may be 0 if pre-treatment core body temperatures are normal or, if not, is generally at least about 0.1, more often at least about 0.5, usually at least about 1.0, sometimes to 2.0, or whatever increase is required to bring the subject substantially to normothermia. As such, the subject methods may be used to increase the core body temperature of the mammal to a temperature ranging from about 37 to 44° C., usually from about 38 to 40° C.

Apparatus 100 may be used to treat a variety of conditions believed to arise from deficiencies of the circulatory, lymphatic and endocrine systems, and which may beneficially impact neurological deficits as well. It is expected, for example, that use of the apparatus of the present invention may treat or alleviate a variety of ailments, including: improved healing for chronic wounds and post-operative conditions; provide relief for respiratory conditions such as asthma; sleeping conditions such as snoring and sleep apnea; metabolic disorders such as hypothyroidism; obesity; chronic fatigue syndrome; certain autoimmune disorders; Raynaud's phenomenon; hot flashes; edema; renal disease; cirrhosis; allergies; neurological maladies such as Parkinson's disease, diabetic neuropathy, migraines, Alzheimer's disease, bipolar disorder, schizophrenia, attention deficit disorder (ADD), attention deficit hyperactivity disorder (ADHD), obsessive compulsive disorder (OCD), and Autism; circulatory disorders associated with vasoconstriction such as hypertension, carpal tunnel syndrome, trigger finger, and arthritis; diabetes; dermatological disorders associated with restricted blood flow to the skin such as eczema; disorders known to disrupt thermoregulatory processes such as stress and anxiety; neurodegenerative conditions such as multiple sclerosis and fibromyalgia; and sequalae of chemotherapy (affecting digestion). Apparatus 100 also may be used to enhance delivery of drugs by increasing body circulation.

In operation, a user or clinician activates apparatus 100 using control panel 103 and selects a heating or cooling mode, or if available, one a plurality of preprogrammed therapeutic regimes. Tubular sleeve 104 is placed over the user's appendage, e.g., hand, arm, foot, or leg, or the user inserts their appendage into tubular sleeve 104 having end 104B placed over rim 108 and firmly held in place using an elastic band or VELCRO® straps, if provided. The appendage then is positioned within the appendage chamber, e.g., appendage chamber 101, and the chamber is closed, if necessary. The upper portion of the appendage chamber may be fastened to the lower portion using quick release buckles or VELCRO® straps, if provided. Second end 104B of tubular sleeve 104 may be placed over a rim of the appendage chamber, if necessary. Alternatively, for the embodiment of FIG. 2B, first end 104A' of the sleeve may be everted over rim 108. Optional bladder 114 then may be inflated to urge the palm of the user's hand against the thermal exchange member, until a desired pressure is attained in bladder 114 under control of programmable controller. Alternatively, the hand may be allowed to rest on the thermal exchange member by operation of gravity and pressure within the appendage chamber. Vacuum is drawn in the appendage chamber at, for example, 25 mm Hg to 35 mm Hg, using the vacuum source located in housing 102 to maintain vasodilation within the appendage. Thermal exchange member 113 is cooled or heated to deliver normothermic heating or cooling, e.g., heating or cooling a person having a normal body temperature pre-treatment, to the appendage at a temperature and for a duration sufficient to alleviate symptoms associated with the condition. Upon completion of the treatment, the programmable controller shuts of the medium source, shuts off vacuum source, and deflates bladder 114, if provided. The user may then break the vacuum seal by opening first end 104A of tubular sleeve 104 or by pulling second end 104B off rim 108, thereby enabling the user to withdraw the appendage from the chamber.

As discussed above, the methods and apparatus of the present invention are intended to create vasodilation of an arteriovenous anastomosis vascular area in a mammal, deliver heat to a body core of the mammal using the dilated arteriovenous anastomosis vascular area, and may continue to deliver heat to the body core using the dilated arteriovenous anastomosis vascular area to a body at normothermia pre-treatment or to a body at sub-normothermia pre-treatment such that the body core reaches normothermia. Applicant believes that continuing to deliver heat to the dilated arteriovenous anastomosis area to a body at normothermia, or to a body core that has reached normothermia, causes secondary vasodilation in other arteriovenous anastomosis and peripheral vascular areas throughout the entire body to dissipate the excess heat being infused by the apparatus. The rapid delivery by the circulatory system of the blood needed to fill these newly dilated heat exchange-vascular structures increases microvascular circulation, benefitting all organs (internal and peripheral) and the associated neurological, lymphatic and endocrinal systems.

It is also expected that the methods and apparatus of the present invention may be used to treat a variety of neurological maladies that have not previously been identified as treatable by the therapeutic application of thermal energy. For example, it is expected that use of apparatus constructed in accordance with the principles of the present invention causes enhanced systemic circulation, which in turn causes redistribution of intracranial and peripheral blood flow. Without wishing to be bound by such theory as to the mechanism of action, it is expected that such redistribution may lead to varied flow patterns in the brain, e.g., in the circulation in the Circle of Willis, thereby alleviating symptoms of neurological maladies such as Parkinson's disease, migraines, Alzheimer's disease, bipolar disorder, schizophrenia, attention deficit disorder (ADD), attention deficit hyperactivity disorder (ADHD), obsessive compulsive disorder (OCD), and Autism.

It is also expected that increased circulation resulting from use of apparatus constructed in accordance with the present invention will provide several important benefits to patients suffering from poor peripheral circulation. For example, diabetic patients who maintain poor blood glucose control are known to suffer from poor peripheral blood circulation and neuropathy, often resulting in limb amputation, especially of toes. It is expected that treatments provided using the apparatus of the present invention will increase peripheral circulation in diabetic patients, thereby reducing the risk of occurrence of gangrene requiring amputation. In addition, the enhanced peripheral circulation is expected to reduce neuropathy in such patients, which further reduces the risk of injury to peripheral limbs and appendages necessitating amputation.

It is expected that use of the methods and apparatus of the present invention also may promote wound healing by stimulating the lymphatic system. In particular, delivering heat to a normothermic person (a person having approximately normal body temperature) has been observed to increase whole body circulation. While not wishing to be bound by any theory as to the mechanism of action, it is believed that such increased circulation will also stimulate the lymphatic and endocrinal systems. With respect to the lymphatic system, which controls transmission of intracellular fluids, an increase in blood circulation also is expected to produce a corresponding increase in flow in the lymph system. For a patient suffering from chronic wounds, such as diabetic ulcers, stimulation of the lymphatic system is expected to improve flow of exudate to the site of the chronic wound. Provided that steps are taken to prevent pooling of exudate at the wound site (e.g., to prevent bacterial growth), such increased exudate is expected to wash toxins from the wound bed, and more quickly deliver materials (platelets and proteins) to the wound site that facilitate wound hearing.

Improved functioning of the lymph system resulting from use of the apparatus of the present invention also may be beneficial for patients suffering from edema, for example, resulting from end-stage renal disease or cirrhosis of the liver. In such patients, hypertension resulting from declining kidney function and/or reduced liver function due to cirrhosis can result in the buildup of excess interstitial fluid in the abdomen and legs. It is believed that by increasing whole body circulation in accordance with the present invention, multiple benefits may be achieved. First, increased whole body circulation is expected to lead to vasodilation of peripheral vessels, thereby allowing blood to fill those vessels and reduce hypertension. Second, the increased blood flow is expected to stimulate the lymphatic system, possibly facilitating the removal and processing of interstitial fluids and reducing edema. While believed to be curative, use of the apparatus of the present invention with such patients on a regular basis, e.g., once or twice per week, may be palliative and improve the patient's quality of life.

While not wishing to be bound by any theory as to the mechanism of action, the present invention is believed to affect core body temperature by opening one or more arteriovenous anastomoses (AVAs) in the subject's body by applying a temperature gradient that exchanges heat in blood in the AVA that is circulated by the heart. Thermoregulatory feedback mechanisms are likely also implicated, by stimulating heat transfer at the core and/or head in response to increases in temperature elsewhere in the body. Whatever the mechanism of action, use of the invention to apply heat to the skin at a location on the body remote from the intended treatment site (e.g., to the extremities to thermoregulate core or cranial temperatures) produces heat transfers at the body core to therapeutic levels.

It is further believed that use of the methods of the invention will have an effect on metabolic processes in the body by affecting the activity of certain enzymes and hormones. For example, the thermoregulatory changes produced by use of the invention may influence the activity of enzymes involved in pain, such as prostaglandin-E synthesizing (PEGS) enzymes, COX enzymes (1, 2 and/or 3), and/or microsomal PEGS-1 (mPEGS), most likely by increasing enzyme kinetics slowed by abnormally low core body temperatures. In metabolic disorders such as hypothyroidism, the body temperature is lowered and enzyme function decreases, slowing metabolism and leading to weight gain and fatigue. Raising body temperature according to the invention may restore the enzymes' kinetic rate and positively affect metabolic disorders.

Patients in a pre-diabetic or diabetic state, as clinically measured from blood glucose and/or A1C levels in the subject over time, may experience increased weight loss using of the methods of the invention. Again, while not wishing to be bound by any theory as to mechanism of action, the potential impact on metabolic processes as described herein may be in play in pre-diabetic and diabetic individuals, in whom core body temperatures may become sub-normothermic over time or normothermic individuals that may benefit from increased circulation.

The biological responses produced by use of the invention have therapeutic implications for a further range of conditions. For example, migraines, chronic fatigue syndrome, and certain autoimmune disorders share symptoms with autonomic and sympathetic nervous system (SNS) hypofunction. The SNS controls blood vessel constriction, decreasing blood flow to extremities when activated. Warmed blood from the heart will first warm the SNS nerve nexus behind the heart. This SNS influence may then reverse the SNS hypofunction and in turn reverse the symptoms of the condition being treated. Therefore, in preferred embodiments, the invention may be used to treat migraines and also to reduce the incidence of pre-migraine events, such as prodomes and auras.

Thermal energy also may to be removed from the head to provide beneficial effects. In some embodiments, thermal energy is removed from the head arterial blood supply, e.g., carotid arterial blood. Those of ordinary skill in the clinical arts will be familiar with or may readily ascertain other measures for beneficial improvements in the condition of treated patients; e.g., reductions in body mass, improvements in neurological function as evidenced by motor function test results, and the like.

In addition, circulatory disorders associated with vasoconstriction in the extremities (such as carpal tunnel syndrome, trigger finger and arthritis) may be treated. Treatment of dermatological disorders associated with restricted blood flow to the skin (such as eczema) may also be effected by increasing the local flow of blood and oxygen to a treatment site. Disorders known to disrupt thermoregulatory processes such as stress, anxiety, neurodegenerative conditions such as multiple sclerosis and fibromyalgia, as well as sequalae of chemotherapy (affecting digestion) may also be beneficially affected by use of the invention.

The above described thermal energy treatments may be performed with or without the aid of automated data collection devices and/or processors. As such, in certain embodiments one or more sensors are employed to detect temperatures in the core body and head region of the mammal. Any convenient temperature sensing devices may be employed, where suitable devices include: thermocouples, thermistors, microwave temperature sensors, infrared cameras, and the like. The position and nature of the temperature sensing devices necessarily depends on whether it is to detect the core body or head temperature of the mammal. For detecting thoracic/abdominal core body temperature, sensor locations of interest include: the esophagus, the rectum, and in the case of microwave detection, anywhere on the surface of the body to measure the underlying temperature. For head temperature, sensor locations of interest include: the auditory canal, the oral cavity, and in the case of microwave detection, anywhere on the surface of the head to measure the underlying temperature.

The data collected from these sensor devices may be processed by a processor to at least display the data for the operator in a user friendly/readable format. The data may also be processed by a processor which causes or inhibits the thermal energy transfer events in response to the detected data or variations therein.

Examples of the practice of the invention are set forth below. These examples shall not be considered to limit the invention, whose scope is defined by the appended claims.

EXAMPLE 1

Treatment of Migraine Headache and Pre-Migraine Symptoms

Figure 7A:
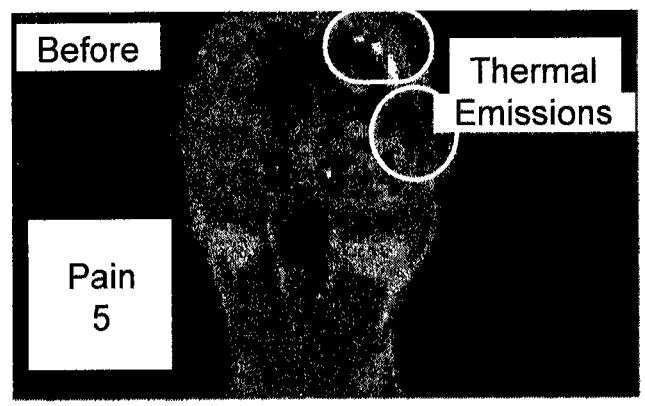
FIGS. 7A through 7C are a series of images obtained by infrared camera depicting changes in core body temperature at the head of a migraine patient treated in accordance with the methods of the present invention.
Figure 7B:
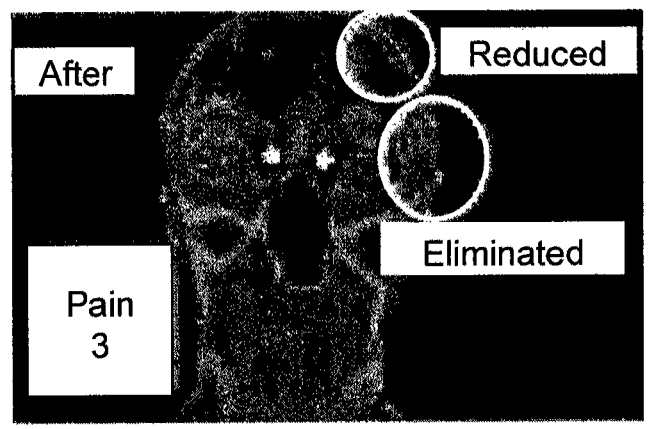
Figure 7C:
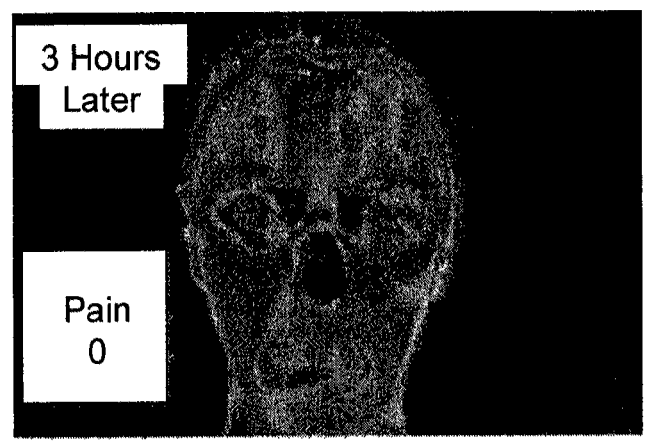

A beneficial improvement in the condition of human patients treated for migraine was confirmed both by patient reports of reductions in the incidence of adverse symptoms (e.g., premonitory events, pain and nausea) as well as by infrared camera detection of changes in body temperature at the hands and head (including the neck) associated with vasodilation as shown in FIGS. 7A through 7C. FIGS. 7A through 7C are a series of images obtained by infrared camera depicting changes in core body temperature at the head of migraine patient number 5 in the Table below treated in accordance with the methods of the present invention.

FIG. 7A shows a thermal image taken immediately prior to treatment of a patient with an active migraine headache; FIG. 7B shows a thermal image taken following completion of a 7 minute treatment; and FIG. 7C shows a thermal image taken 3 hours thereafter. In the images, the whitest areas are hottest, the dark gray are the next hottest, and the light gray are the least hot. The white areas near the skull shown in FIG. 7A are gone after treatment as shown in FIG. 7B and all white areas are gone 3 hours after treatment as shown in FIG. 7C.

In the study of patients treated for migraines, each of the adult human volunteers for whom results are recited below was treated for a continuous period of 10 minutes through application of thermal energy at 43° C. under an average pressure of 30 mmHg. The "Results" section of the Table below is based on verbal feedback from the treated patients.

|    | Age | Gender | Stage* | Result |
|----|-----|--------|--------|--------|
| 1  | 65  | Female | Migraine | Migraine prevented. 20 year weekly sufferer cured in 4 months |
| 2  | 45  | Female | Migraine | Relief in 30 min. |
| 3  | 65  | Female | Aura | Migraine prevented |
| 4  | 55  | Male | Aura | Migraine prevented |
| 5  | 20  | Female | Migraine | Immediate relief. No sign after 3 hours |
| 6  | 50  | Female | Migraine | Immediate relief |
| 7  | 35  | Male | Migraine | Immediate relief |
| 8  | 27  | Female | Migraine | Immediate relief. Eating again (21 days) |
| 9  | 43  | Female | Aura | Migraine prevented. Repeated 3 consecutive days |
| 10 | 35  | Female | Prodome | Migraine prevented |
| 11 | 50  | Female | Migraine | Immediate relief |
| 12 | Adult | Male | Migraine | No relief with 10 min. cooling. Then 90% relief 18" after warming |
| 13 | Adult | Female | Migraine | 2 hours into migraine when treated. Immediate clearing relief in head. Pain reduction |
| 14 | Adult | Female | Prodome | Prevented migraine onset. Repeated with same results on three separate events over three days |

*Stages: Prodome, Aura, Migraine Headache

EXAMPLE II

Weight Loss

A patient reported 20% weight loss when undergoing two warming treatments per day, upon waking and prior to bed, in accordance with the present invention.

EXAMPLE III

Autism, OCD, and ADD

A caretaker of a patient having Autism, ADD, and OCD reported increased calmness, improved attention, and improved language skills in the patient when undergoing one to two warming treatments per day, in accordance with the present invention.

EXAMPLE IV

Fibromyalgia

Three patients having fibromyalgia reported decreased pain and increased ability for activity when undergoing one to two warming treatments per day, in accordance with the present invention.

EXAMPLE V

Chronic Wound

A patient having a post-operative wound that became infected reported healing after 3 months when undergoing one to two warming treatments per day, in accordance with the present invention. Prior to the warming treatments, the following treatments were unsuccessful: wearing a wound vacuum for months; 40 hyperbaric treatments 5 days per week, 1½ hours per day, for 8 weeks; and 4 skin grafts on the wound.

EXAMPLE VI

Diabetic Wounds

A patient having diabetic wounds and loss of circulation in appendages reported healing of the diabetic wounds and warming and feeling in the appendages when undergoing two warming treatments per day, in accordance with the present invention.

EXAMPLE VII

Growth of Fingernails

A patient having fingernail loss reported growth of the fingernails for the first time in years when undergoing one warming treatments per day, in accordance with the present invention.

EXAMPLE VIII

Post-Surgery Pain, Allergies, and Snoring

A patient having two ACL knee surgeries, allergies, and snoring reported decreased pain, decreased allergy symptoms, and decreased snoring when undergoing one to two warming treatments per day, in accordance with the present invention.

EXAMPLE IX

Parkinson's Disease

A patient having Parkinson's disease reported decreased severity of tremors, improved speech, improved motor skills, long-term memory improvement when undergoing one to two warming treatments per day, in accordance with the present invention.

Suggested Protocols for Treatment of Conditions

Suggested treatment protocols of 10 minutes, twice per day (preferably upon waking and before bed), at the heating mode are recommended for the following conditions: chronic wounds; post-operative conditions; respiratory conditions such as asthma; sleeping conditions such as snoring and sleep apnea; metabolic disorders such as hypothyroidism; obesity; chronic fatigue syndrome; certain autoimmune disorders; Raynaud's phenomenon; hot flashes; edema; renal disease; cirrhosis; allergies; neurological maladies such as Parkinson's disease, diabetic neuropathy, migraines, Alzheimer's disease, bipolar disorder, schizophrenia, attention deficit disorder (ADD), attention deficit hyperactivity disorder (ADHD), obsessive compulsive disorder (OCD), and Autism; circulatory disorders associated with vasoconstriction such as hypertension, carpal tunnel syndrome, trigger finger and arthritis; diabetes; dermatological disorders associated with restricted blood flow to the skin such as eczema; disorders known to disrupt thermoregulatory processes such as stress and anxiety; neurodegenerative conditions such as multiple sclerosis and fibromyalgia; and sequalae of chemotherapy (affecting digestion).

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. Apparatus for treating a condition of a human, the apparatus comprising:
    an appendage chamber configured to accept a human hand, the chamber having an upper portion, a lower portion, and an appendage opening;
    a thermal exchange member disposed within only the lower portion, the thermal exchange member configured to contact a palm of the hand to selectively heat or cool the palm of the hand;
    a pressure sensor disposed under the thermal exchange member, the pressure sensor configured to measure a pressure of the hand against the thermal exchange member;
    wherein the measured pressure is used to determine if the pressure of the hand is within a predetermined range;
    a tubular sleeve having a first open end, the sleeve configured to accept a human arm, wherein the tubular sleeve is detachably coupled to the appendage chamber;
    a vacuum source coupled to the appendage chamber to maintain vasodilation of the hand when placed within the appendage chamber; and
    a programmable controller configured to monitor the pressure measured using the pressure sensor, to control the application of vacuum to the appendage chamber, and to control heating or cooling of the thermal exchange member to effect normothermic heating or cooling responsive to a preselected therapy regime.

2. The apparatus of claim 1, wherein the programmable controller includes memory for storing a plurality of programs that may be selected to implement the preselected therapy regime.

3. The apparatus of claim 1, further comprising a control panel that enables input of selected parameters to effectuate the preselected therapy regime.

4. The apparatus of claim 1, wherein the preselected therapy regime is configured to treat a neurological malady such as Parkinson's disease, diabetic neuropathy, migraines, Alzheimer's disease, bipolar disorder, schizophrenia, attention deficit disorder (ADD), attention deficit hyperactivity disorder (ADHD), obsessive compulsive disorder (OCD), Autism, or any combination thereof.

5. The apparatus of claim 1, wherein the preselected therapy regime is selected to alleviate a symptom associated with a circulatory, neurological, lymphatic, or endocrinal dysfunction, or any combination thereof.

6. The apparatus of claim 1, wherein the apparatus is configured to promote healing of a chronic wound.

7. The apparatus of claim 1, wherein the pressure sensor comprises a load cell configured to measure the pressure of the hand against the thermal exchange member.

8. The apparatus of claim 1, further comprising an inflatable bladder disposed within the upper portion, and
    wherein the programmable controller is further configured to inflate the inflatable bladder to a preselected pressure.

9. The apparatus of claim 8, further comprising a pressure sensor configured to measure pressure of the inflatable bladder.

10. The apparatus of claim 1, further comprising a temperature sensor configured to measure temperature at the thermal exchange member.

11. A method for treating a condition of a human, the method comprising:
    providing an appendage chamber, a thermal exchange member disposed within the appendage chamber, and a vacuum source coupled to the appendage chamber;
    disposing an appendage within the appendage chamber in contact with the thermal exchange member;
    creating a vacuum in the appendage chamber using the vacuum source to induce vasodilation within the appendage;
    measuring a pressure of the appendage against the thermal exchange member; monitoring the measured pressure;
    wherein the measured pressure is used to determine if the pressure of the appendage is within a predetermined range; and
    heating the thermal exchange member to deliver normothermic heating or cooling to the appendage at a temperature and for a duration sufficient to cause an increase in whole body circulation and alleviate a symptom associated with at least one of a circulatory, neurological, lymphatic, or endocrinal malady.

12. The method of claim 11, wherein the increase in whole body circulation causes redistribution of intracranial flow to alleviate symptoms associated with migraine headache.

13. The method of claim 11, wherein the heating comprises heating the thermal exchange member to deliver normothermic heating or cooling to the appendage for approximately five to twenty minutes.

14. The method of claim 11, wherein the heating comprises heating the thermal exchange member to approximately 43° C. to deliver normothermic heating or cooling to the appendage.

15. The method of claim 11, wherein the method is performed at least once a day.

16. The method of claim 11, where the method is performed at least twice daily.

17. The method of claim 11, wherein the symptom comprises the persistence of a chronic wound, the increase in whole body circulation stimulating exudate generation at the chronic wound.

18. The method of claim 11, wherein the increase in whole body circulation alleviates the symptom associated with one of Parkinson's disease, diabetic neuropathy, migraines, Alzheimer's disease, bipolar disorder, schizophrenia, attention deficit disorder (ADD), attention deficit hyperactivity disorder (ADHD), obsessive compulsive disorder (OCD) and Autism.

19. The method of claim 11, wherein the increase in whole body circulation reduces one or more of edema size, duration, or formation associated with kidney or liver dysfunction.

20. The method of claim 11, wherein the increase in whole body circulation reduces symptoms associated with operation of a human menstrual cycle.

21. The apparatus of claim 1, wherein the tubular sleeve further comprises a second open end, wherein one of the first and second ends is disposed over a rim of the appendage opening.

22. The apparatus of claim 1, wherein the tubular sleeve further comprises a second end that forms a pouch or mitt.

23. The apparatus of claim 22, further comprising a plurality of holes disposed in a portion of the pouch or mitt.

* * * * *